US00PP08298P

United States Patent [19]

Newby, Jr. et al.

[11] Patent Number: Plant 8,298

[45] Date of Patent: Jul. 13, 1993

[54] GRAPEVINE CV. SUGRATWELVE

[75] Inventors: Harry J. Newby, Jr., Mecca; David W. Cain; Kevin S. Andrew, both of Bakersfield, all of Calif.

[73] Assignee: Sun World, Inc., Coachella, Calif.

[21] Appl. No.: 811,582

[22] Filed: Dec. 20, 1991

[51] Int. Cl.[5] ..... A01H 5/00

[52] U.S. Cl. ..... Plt./47.3

[58] Field of Search ..... Plt./47.3

[56] References Cited

U.S. PATENT DOCUMENTS

P.P. 3,106 4/1972 Garabedian ..... Plt. 47.3

P.P. 5,151 12/1983 Hahn et al. ..... Plt. 47.3

*Primary Examiner*—James R. Feyrer

*Attorney, Agent, or Firm*—Synnestvedt & Lechner

[57] ABSTRACT

A grapevine cv. Sugratwelve that is a mutation of the Sugraone grapevine and that is characterized by its seedless grapes which mature two days earlier than Sugraone grapes and differ markedly from Sugraone grapes in cluster count per vine, cluster weight, berry weight, berry length, berry diameter, sugar content and titratable acid levels.

2 Drawing Sheets

This invention relates to the discovery and asexual propagation of a new variety of hybrid grapevine *Vitis vinifera* cv. Sugratwelve. The Sugratwelve variety bears seedless berries that have a pleasing taste and other desirable table grape characteristics. The Sugratwelve variety was discovered by Harry Joe Newby, Jr., as a single cordon mutation of a Sugraone grapevine (U.S. Plant Pat. No. 3,106) growing in a commercial vineyard near Thermal, Calif. David W. Cain and Kevin S. Andrew asexually propagated the new variety from a cutting taken from the mutation and demonstrated its stability from hardwood cuttings and graftings. The Sugratwelve grapevine maintains its distinguishing characteristics as hereinafter set out through successive asexual propagations using hardwood cuttings and grafting techniques.

The new Sugratwelve variety may be distinguished from its parent Sugraone and also from other presently available commercial cultivars by the following combination of characteristics: it matures at about the same time (about two days earlier) as Sugraone and about 10 to 15 days before the Thompson Seedless variety; the berries are somewhat similar in shape to those of the Thompson Seedless variety and are more elongated in shape than those of the Sugraone and Perlette varieties. The fruit has a tougher skin and a more crisp flesh texture and a lighter greenish creamy white skin color than either Thompson Seedless or Centennial Seedless which tend to have a deeper green skin color. As will be described in greater detail hereinafter, the Sugratwelve and Sugraone grapevines and fruit differ markedly as to cluster count per vine, cluster weight, berry weight, berry length, berry diameter, sugar content and titratable acid levels.

Figure 1:
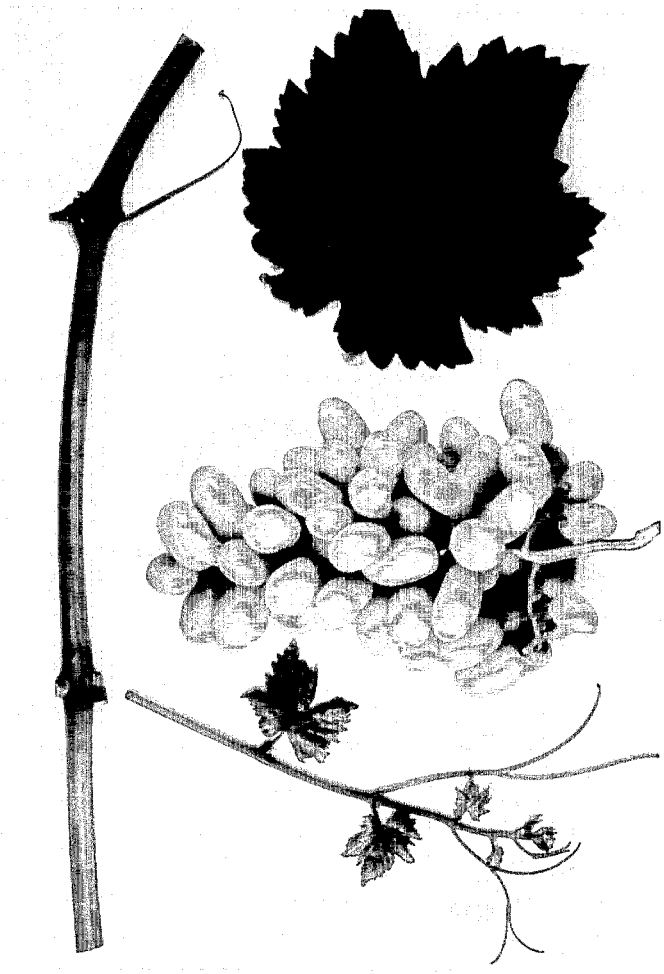
Figure 2:
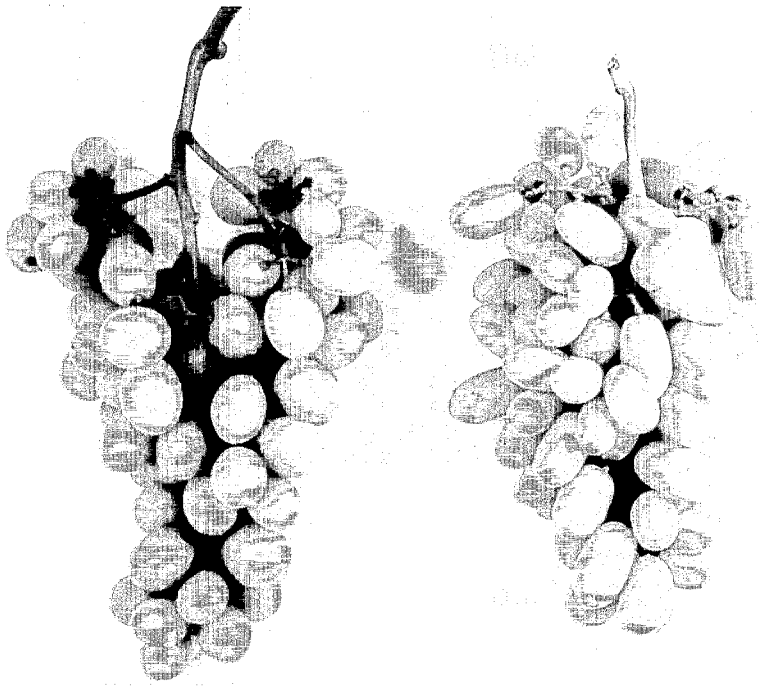

In the accompanying drawings, FIG. 1 illustrates, in full color, a typical cluster of berries, stem section, young shoot and mature leaf blade of the new grapevine. FIG. 2 illustrates a Sugraone variety berry cluster (on left) and a Sugratwelve variety berry cluster (on right).

Throughout this specification, color names beginning with a small letter signify that the name of the color, as used in common speech, is aptly descriptive. Color names beginning with capital letters designate values based on The R.H.S. Colour Chart of The Royal Horticultural Society of London, England.

The descriptive matter which follows pertains to grapevines of the new Sugratwelve variety grown near Wasco, in Kern County, Calif., in 1990 and 1991, and is believed to apply to plants of the variety grown under similar conditions of soil and climate elsewhere.

VINE

The vine on its own root is large in size and of medium vigor. The foliage is of medium density. The vines are hardy, productive, bearing their fruit regularly.

The trunk is of average thickness and bears long straps. The surface is of medium texture and about Greyed-Orange 174C in color. The canes are average in caliper and are of medium surface texture. Canes are about 180 cm. long and about 1.5 cm. wide at the node. Nodes are rounded and of average length. The average distance between nodes is about 7 cm.

SHOOTS

Shoots exhibit strong vigor during flowering. Flowering shoots are semi-erect when not tied. The dorsal and ventral sides of both the internodes and nodes are green with red stripes, about Greyed-Purple 183B in color. Anthocyanin coloration is absent from or very weak in the immature shoot buds.

Young shoot tips are half-open in form. Very weak anthocyanin coloration is distributed as piping at the edges of the young shoot tips. Both prostrate and erect hairs are present in average densities at the shoot tips.

Woody shoots are circular in cross section. The surface of woody shoots is ribbed and about Greyed-Orange 165D in color.

Lenticels are absent. Erect hairs are dense at the nodes and no hairs are present at the internodes.

Tendrils, averaging about 20 cm. in length and medium thickness are discontinuously distributed on the shoot at full flower. Tendrils are about Yellow-Green 145B in color. Tendrils are trifurcated in form.

Leaf producing buds are slightly pointed and of average size—about 0.4 cm. Buds are markedly held out at an angle of about 60°. Basal buds are unfruitful and mid shoot and distal buds are fruitful and seldom dead.

LEAVES

In general, the upper surface of a young leaf is about Yellow-Green 144A in color. Prior to flowering anthocyanin is weak or absent in the distal leaves. On the lower surface of the young leaves, both prostrate and erect hairs are very sparsely distributed between veins and sparsely on the veins.

Mature leaves have a generally circular outline and an involute profile. Leaves are of average size (about 13 cm. long and about 18 cm. wide) and the blades are of medium size, pentagonal in shape and have 3 lobes. The leaf blade tip lies in the plane of the leaf. The leaf margin shows medium undulation. The leaf apex is cuspidate; the leaf base is V-shaped. The leaf blade has undulations between the main and lateral veins but only near the petiole. Teeth are convex on both sides. The upper leaf sinuses are closed.

The upper surface of the leaf is near Yellow-Green 137A in color. Anthocyanin coloration is absent on the main veins of the upper leaf surface. The upper leaf surface is rugose in texture, weakly glossy and has a dull surface appearance; Pubescence is absent. Blistering on upper side surface of blade is absent or very weak. Blades are goffered.

The lower leaf surface is about Green 137C in color, average in glossiness and with no pubescence. Anthocyanin coloration of the main veins on the lower leaf surface is absent. The lower leaf surface is smooth in texture and semi-glossy in surface appearance.

The petiole is shorter than the middle vein. There are no erect hairs present on the petiole. The petiole sinus has slightly overlapping lobes and V-shaped at the base. There are no particularly distinguishing features with respect to the petiole sinus. The lobes forming the upper leaf sinus are slightly overlapping. The base of the upper leaf sinus is V-shaped. Anthocyanin coloration is absent on the main vein on both the upper or lower blade surfaces.

FLOWERS

The flowers are fertile, of average size and are hardy. They are of average length and plump in shape. Fruit is produced at the 5th to 6th node.

In Wasco, Calif., flowers attained first and full bloom between May 10, 1991 and May 21, 1991, generally the same as the Sugraone, 8 days before Thompson seedless and slightly earlier than most other similar varieties in the growing in this area. Flowers are of average size and length, usually 6 per cane and about 36 per vine. Flowers are hermaphroditic.

FRUIT

The fruit of the new variety ripens about 2 days before fruit of the Sugraone variety and about 15 days ahead of the Thompson Seedless variety.

Fruit is suitable for market use and has average shipping qualities; it has average resistance to insects and diseases.

The size of the berry clusters (excluding the peduncle) is average; weighing on the average about 348 grams. The loosely compact, conical cluster usually bears an average of about 67 to 68 berries.

The peduncle is of average length and shows weak lignification. Peduncle color is near Yellow-Green 145C.

Berries are large, but vary in size and are of cylindrical shape with a circular cross section (on average the longitudinal axis is about 26–27 mm long, and the horizontal axis is about 17 mm in diameter). The brush usually pulls out of the berry without the pedical. Berries are near Yellow-Green 151A in color. When ripe, the berries have a sweet subacidic taste and when very ripe a very faint muscat taste can be noted.

The skin is of average thickness, crisp in texture, is tenacious to the flesh, rough and without reticulation.

Table 1 below provides a comparison of the cluster count, cluster weight, berry weight and berry dimensions of Sugratwelve grapes and Sugraone grapes.

TABLE 1

CHARACTERISTICS OF SUGRATWELVE VS. SUGRAONE

| | SUGRATWELVE MEAN + STANDARD DEVIATION | SUGRAONE MEAN + STANDARD DEVIATION |
|---|---|---|
| Cluster count/vine | 31.5 ± 10.7 | 38.8 ± 7.6 |
| Cluster weight (grams) | 348 ± 65 | 565 ± 104 |
| (pounds) | 0.77 ± 0.14 | 1.24 ± 0.23 |
| Berry weight (grams) | 5.14 ± 0.85 | 5.46 ± 0.95 |
| Berry length (millimeters) | 26.6 ± 1.6 | 22.6 ± 1.24 |
| Berry diameter (millimeters) | 17.2 ± 0.59 | 19.21 ± 0.73 |

Table 2 below tabulates the sugar contents and titratable acid of Sugratwelve grapes and sugraone grapes over a two week ripening period.

TABLE 2

SUGAR AND TITRATABLE ACID LEVELS OF SUGRATWELVE VS. SUGRAONE

| | SUGRATWELVE | | SUGRAONE | |
|---|---|---|---|---|
| DATE | SUGAR °BRIX | ACID G/100 ML | SUGAR °BRIX | ACID G/100 ML |
| 7-12-91 | 14.9 ± 0.78 | 0.76 ± 0.08 | 13.5 ± 1.1 | 0.88 ± 0.07 |
| 7-16-91 | 16.0 ± 0.75 | 0.66 ± 0.07 | 14.2 ± 1.1 | 0.71 ± 0.07 |
| 7-19-91 | 16.4 ± 0.67 | 0.56 ± 0.05 | 14.8 ± 1.0 | 0.59 ± 0.06 |
| 7-22-91 | 16.8 ± 0.66 | 0.52 ± 0.05 | 15.4 ± 1.1 | 0.55 ± 0.06 |
| 7-26-91 | 17.2 ± 0.61 | 0.49 ± 0.04 | 15.9 ± 1.1 | 0.52 ± 0.06 |

What is claimed is:

1. A new variety of grapevine cv. Sugratwelve, substantially as herein shown and described.

* * * * *